(12) United States Patent
Spiess

(10) Patent No.: US 6,967,033 B1
(45) Date of Patent: Nov. 22, 2005

(54) PHARMACEUTICALLY ACTIVE PLANT PREPARATION FOR THE TREATMENT OF MIGRAINE

(75) Inventor: Stefan Spiess, Schaftlach (DE)

(73) Assignee: Hexal AG, Helzkirchen (DE)

(*) Notice: Subject to any disclaimer, the term of this patent is extended or adjusted under 35 U.S.C. 154(b) by 0 days.

(21) Appl. No.: 09/806,558

(22) PCT Filed: Sep. 22, 1999

(86) PCT No.: PCT/EP99/07045

§ 371 (c)(1),
(2), (4) Date: Mar. 30, 2001

(87) PCT Pub. No.: WO00/18415

PCT Pub. Date: Apr. 6, 2000

(30) Foreign Application Priority Data

Sep. 30, 1998 (DE) ................................ 198 44 836

(51) Int. Cl.⁷ ............................................. A61K 35/78
(52) U.S. Cl. ...................... 424/764; 424/725; 424/756; 514/899
(58) Field of Search ................................ 424/725, 756, 424/764; 514/899

(56) References Cited

U.S. PATENT DOCUMENTS 5,443,850 A * 8/1995 Thys-Jacobs
5,466,451 A 11/1995 Beuscher et al.
5,565,199 A * 10/1996 Page et al.

FOREIGN PATENT DOCUMENTS

| DE | 42 02 657 | | 8/1993 |
| EP | 248215 | * | 12/1987 |
| WO | WO 92/11857 | | 7/1992 |
| WO | 96/22774 | * | 8/1996 |
| WO | WO 98/39018 | | 9/1998 |

OTHER PUBLICATIONS

Product Alert. Jul. 22, 1996. Alvita Herbal RemeTeas—Lancaster County Migra-Wonder. PROMT Abstract.*
Castleman, M. 1991. The Healing Herbs. Publ: Rodale Press, Emmaus, PA. pp. 186-189.*
PDR for Herbal Medicines, 1st ed. Spring 1998. Publ: Mecial Econ. Co., Montvale, NJ, pp. 746-748 and 1222-1223.*
Article "A Bioassay For Inhibition of Serotonin Release From Bovine Platelets" by Marles, et al., published in Journal of Natural Products, vol. 55, No. 8, pp. 1044-1056 dated Aug. 1992.
Article "An Herbal Update, Part 2" by Wyandt, et al., published in Drug Topics, Jun. 1, 1998 pp. 66A.

* cited by examiner

Primary Examiner—Christopher R. Tate
(74) Attorney, Agent, or Firm—Cohen, Pontani, Lieberman & Pavane

(57) ABSTRACT

The invention relates to pharmaceutical combination preparations with synergistic action for the treatment of migraine. Said preparations contain plant-based components and/or preparations of *Tanacetum parthenium* in combination with *Vitex agnus castus* and/or *Cimicifuga racemosa* and/or *Zingiber officinale* as their pharmaceutically active ingredients. The combination preparation provided for in the invention is suitable for the treatment of not only the headache but also the other symptoms of migraine while avoiding the usual side-effects.

19 Claims, No Drawings

PHARMACEUTICALLY ACTIVE PLANT PREPARATION FOR THE TREATMENT OF MIGRAINE

BACKGROUND OF THE INVENTION

The invention pertains to a pharmaceutically active herbal preparation with improved effectiveness for the all-encompassing treatment of migraine, the preparation containing plant components and/or preparations of *Tanacetum parthenium* in combination with *Vitex agnus-castus* and/or *Cimicifuga racemosa* and/or *Zingiber officinale* as pharmaceutically active components.

Migraine is understood today as a complex functional disturbance of neuronal and vascular elements of the CNS. The headaches associated with it are apparently induced by an aseptic inflammation of the blood vessels and the dura mater vessels of the brain in association with permeability of the vessel walls for albumin and the release of neurotransmitters such as serotonin and tryptamine. The disorder is characterized by the following sequence of events: vasodilation, activation of the trigeminus, and neurogenic inflammation. Migraine attacks occur abruptly and repeatedly. They involve headaches on one side of the head, which can be associated with various accompanying phenomena: autonomic symptoms such as nausea and vomiting, aversion to light and noise, visual symptoms such as disturbed vision, and also neurological breakdowns such as paralysis or disturbances in language or speech. The symptoms, nausea and vomiting, are caused by the absence of gastrointestinal peristalsis. Most (70%) migraine patients are women. They are more likely to suffer migraine during their menstrual periods. The treatment of migraine has been limited so far to the treatment of the headaches as a way of relieving the patient's discomfort. A more effective and improved treatment of migraine by means of phytopharmaceutical preparations to address the other symptoms of migraine is not known.

*Tanacetum parthenium* (feverfew), which belongs to the Asteraceae family, is a traditional herbal remedy used to treat migraine. The flowering plant and especially the leaves of the English variety of *Tanacetum parthenium* contain ethereal oil, camphor, borneol, pinene, and above all sesquiterpene lactones. Sesquiterpene lactones which have been isolated include michefuscalide, cis-chrysanthenyl [sic; chrysanthemyl?—Tr. Ed.] acetate, and parthenolide, which is the dominant component quantitatively and which therefore can be considered the chief substance. To treat migraine in any meaningful way with a drug, it must be possible to affect the parameters vascular disturbance, pain, and inflammation. The sesquiterpene lactones, especially parthenolide, have an antiphlogistic effect by inhibiting prostaglandin synthesis, improve the flow behavior of the blood by inhibiting platelet aggregation, reduce the release of serotonin, inhibit the release of histamine, and exert a spasmolytic effect. *Tanacetum parthenium* is administered in most cases for the sake of prevention. The psychological and physical symptoms typical of migraine are ameliorated by taking *Tanacetum parthenium*, but they often continue to be a considerable burden on the affected persons, with the result that the quality of life is severely impaired.

The active ingredients not of plant origin used to treat migraine such as sumatriptan, ibuprofen, acetylsalicylic acid, etc., also suffer from the problem that the success of the treatment is often insufficient, and there is also the danger of considerable side effects.

The task of the present invention is to provide a more effective phyto-pharmaceutical drug with improved efficacy for the treatment of migraine and with few if any side effects.

THE INVENTION

The surprising discovery has now been made that the task according to the invention can be accomplished by a combination of *Tanacetum parthenium* with other medicinal plants such as *Vitex agnus-castus* and/or *Cimicifuga racemosa* and/or *Zingiber officinale* (ginger). The combination of *Tanacetum parthenium* with *Zingiber officinale* leads to a significant improvement in efficacy; in addition to the alleviation of the headache, the other symptoms of migraine, including especially vertigo, nausea, and gastrointestinal complaints can also be minimized. The combination of *Tanacetum parthenium* with *Vitex agnus-castus* or *Cimicifuga racemosa* as well as the three-fold combination of *Tanacetum parthenium*, *Zingiber officinale*, and *Vitex agnus-castus* lead to a considerable enhancement of the effect or alleviation of all the symptoms of migraine, especially in women whose migraine attacks are concentrated in the time around their periods.

*Vitex agnus-castus* (monk's pepper, chaste tree) belongs to the Verbenaceae family (vervain, verbena). The fruits are the part of the plant which is used. Various secondary plant compounds have been detected as constituents such as iridoids, flavonoids, and ethereal oils. The ability of these compounds to direct their attack against lactotropic cells and to bind themselves to the dopamine receptors there explains why they are so effective in relieving premenstrual syndrome. The term "premenstrual syndrome" is understood to mean a recurring set of psychological and physical disturbances and/or changes in behavior, which normally can occur only in the corpus luteum phase of the menstrual cycle. The increase in prolactin secretion associated with this disorder is significantly reduced by the phytopharmaceutical of the invention. An excessive level of prolactin in the blood lowers pulsatile [?—Tr. Ed.] gonadotropin secretion, which is ultimately the key factor in determining a normal menstrual cycle.

*Cimicifuga racemosa* (snake root, bugbane) belongs to the Ranunculaceae family. The root is the part used for pharmaceutical purposes. The valuable constituents are the triterpene glycosides, especially the xylosides actein and cimicifugoside. The preparation made from the plant material has hormone-like properties, the estrogenic activity component being especially dominant. These herbal preparations are usually used to treat premenstrual syndrome and climacteric symptoms.

*Zingiber officinale* (ginger) is important throughout the world as a spice and as basic material in the food industry, but has also been used medicinally for centuries. It is the root of the *Zingiber officinale* plant which is used pharmaceutically; it contains up to 3% of ethereal oil (ginger oil), the chief components of which quantitatively are sesquiterpene hydrocarbons and sesquiterpene alcohols, primarily zingiberene (30%) and β-bisabolene (10–15%). In addition, it also contains various acrid compounds such as gingerols and shogaols, which are highly effective therapeutically. *Zingiber officinale* is used in modern Western medicine chiefly in the form of powders, extracts, distillates, infusions, tinctures, and the ethereal *Zingiber officinale* oil. It is used to prevent the symptoms of travel sickness, but also quite generally as an antiemetic. In addition, *Zingiber officinale* is used as a carminative, a spasmolytic, an antiflatulent, a digestive, an aperitive, a stomachic, an expectorant, and antitussive, an astringent, a stimulant, and a tonic.

The term "plant components" used here refers to the parts of plants which are used pharmaceutically and which thus contain the active ingredients, such parts being, for example, the leaves, fruits, and roots, including their dried forms.

The herbal preparations can be in the form of extracts, powders, distillates, infusions, tinctures, and oils.

The herbal preparation according to the invention can be in the form of capsules, film-coated tablets, solutions, sugar-coated tablets, suppositories, effervescent tablets, chewable tablets, or effervescent granulate.

The amount of the plant components used in the herbal preparation according to the invention, i.e., the amount of the preparation of *Tanacetum parthenium*, is selected so that it corresponds to 0.1–1 mg, and especially 0.2–0.6 mg, of parthenolide.

The amount of plant components or of the preparation of *Cimicifuga* used in the herbal preparation according to the invention is 20–100 mg.

The amount of plant components or of a preparation of *Vitex agnus-castus* used in the herbal preparation according to the invention is 20–100 mg, where preferably an amount of 20–40 mg is used.

The amount of plant components or of a preparation of *Zingiber officinale* used in the herbal preparation according to the invention is 0.5–6 g, where preferably an amount of 1–4 g is used.

The use of the herbal preparation according to the invention, which contains plant components and/or preparations of *Tanacetum parthenium* in combination with additional plant components selected from the group consisting of *Vitex agnus-castus* and/or *Cimicifuga racemosa* and/or *Zingiber officinale*, is intended for the treatment or prevention of migraine, especially in women in association with their periods, or of menstrual complaints or of additional gastrointestinal complaints.

*Tanacetum parthenium* combined with *Vitex agnus-castus*, *Tanacetum parthenium* combined with *Cimicifuga racemosa*, *Tanacetum parthenium* combined with *Zingiber officinale*, and *Tanacetum parthenium* combined with *Vitex agnus-castus* and *Zingiber officinale* represent the preferred combination preparations according to the invention with respect to the use described above.

The terms and expressions which have been employed are used as terms of description and not of limitation, and there is no intention in the use of such terms and expressions of excluding any equivalent of the features shown and described or portions thereof, it being recognized that various modifications are possible within the scope of the invention.

What is claimed is:

1. An herbal pharmaceutical preparation for the treatment of migraine, comprising: *Tanacetum parthenium*, present in an amount of 0.1–1 mg, of parthenolide, and at least one other component selected from the group consisting of *Vitex agnus-castus*, present in an amount of 20–100 mg, and *Cimicifuga racemosa*, present in an amount of 20–100 mg.

2. The herbal pharmaceutical preparation for the treatment of migraine of claim 1, wherein at least one of the components is in the form of an extract, powder, distillate, infusion, tincture, or oil and the preparation is in the form of a capsule, a film coated tablet, a solution, a sugar-coated tablet, a suppository, an effervescent tablet, a chewable tablet, or an effervescent granulate for administration.

3. The herbal pharmaceutical preparation for the treatment of migraine of claim 1, wherein the least one other component is *Vitex agnus-castus*.

4. The herbal pharmaceutical preparation for the treatment of migraine of claim 1, wherein the least one other component is *Cimicifuga racemosa*.

5. The herbal pharmaceutical preparation for the treatment of migraine of claim 3, further comprising *Zingiber officinale*, in an amount of 0.5–6 g.

6. The herbal pharmaceutical preparation for the treatment of migraine of claim 4, further comprising *Zingiber officinale*, in an amount of 0.5–6.

7. A method for treating or reducing the risk of a migraine in a subject in need thereof, comprising: administering to said subject a preparation of *Tanacetum parthenium*, present in an amount of 0.1–1 mg of parthenolide, in combination with at least one other component selected from the group consisting of *Vitex agnus-castus*, present in an amount of 20–100 mg, and *Cimicifuga racemosa*, present in an amount of 20–100 mg.

8. The method of claim 7 wherein said subject is a woman and the migraine is in association with her period, or of menstrual complaints.

9. The method of claim 7 wherein the preparation is selected from the group consisting of (a) *Tanacetum parthenium* combined with *Vitex agnuscastus*, (b) *Tanacetum parthenium* combined with *Cimicifuga racemosa*, and (c) preparation (a) or (b) combined with *Zingiber officinale* in an amount of 0.5–6 g.

10. The method of claim 7 further comprising *Zingiber officinale* in an amount of 0.5–6 g.

11. The method of claim 7 wherein the preparation is administered in the form of a capsule, a film coated tablet, a solution, a sugar-coated tablet, a suppository, an effervescent tablet, a chewable tablet, or an effervescent granulate.

12. The herbal pharmaceutical preparation for the treatment of migraine of claim 1, wherein the *Tanacetum parthenium* is present in an amount of 0.2 to 0.6 mg. of parthenolide.

13. The herbal pharmaceutical preparation for the treatment of migraine of claim 1, wherein the *Vitex agnus-castus* is present in an amount of 20 to 40 mg.

14. The herbal pharmaceutical preparation for the treatment of migraine of claim 5, wherein the *Zingiber officinale* is present in an amount of 1 to 4 g.

15. The method of claim 7 wherein the amount of the *Tanacetum parthenium* is 0.2 to 0.6 mg. of parthenolide.

16. The method of claim 7 wherein the amount of the *Vitex agnus-castus* is 20 to 40 mg.

17. The method of claim 10 wherein the amount of the *Zingiber officinale* is 1 to 4 g.

18. The herbal preparation of claim 1 wherein said at least one other component is *Cimicifuga racemosa*.

19. An herbal pharmaceutical preparation for the treatment of migraine, comprising: *Tanacetum parthenium*, present in an amount of 0.1–1 mg. of parthenolide, *Vitex agnus-castus*, present in an amount of 20–100 mg, and *Cimicifuga racemosa*, present in an amount of 20–100 mg.

* * * * *